US006872845B2

(12) United States Patent
Westmeyer et al.

(10) Patent No.: US 6,872,845 B2
(45) Date of Patent: Mar. 29, 2005

(54) PROCESS FOR MAKING HALOORGANOALKOXYSILANES

(75) Inventors: Mark D. Westmeyer, Marietta, OH (US); Michael R. Powell, New Martinsville, WV (US); Frank D. Mendicino, Marietta, OH (US)

(73) Assignee: General Electric Company, Pittsfiled, MA (US)

( * ) Notice: Subject to any disclaimer, the term of this patent is extended or adjusted under 35 U.S.C. 154(b) by 30 days.

(21) Appl. No.: 10/378,347

(22) Filed: Mar. 3, 2003

(65) Prior Publication Data

US 2004/0176627 A1 Sep. 9, 2004

(51) Int. Cl.$^7$ .................................................. C07F 7/04
(52) U.S. Cl. ........................................ 556/476; 556/466
(58) Field of Search ............................... 556/466, 476, 556/470

(56) References Cited

U.S. PATENT DOCUMENTS

| | | |
|---|---|---|
| 3,795,656 A | 3/1974 | Martin |
| 4,658,050 A | 4/1987 | Quirk et al. |
| 4,740,607 A | 4/1988 | Bokerman et al. |
| 4,762,939 A | 8/1988 | Mendicino |
| 4,999,446 A | 3/1991 | Moody et al. |
| 5,084,590 A | 1/1992 | Ritscher et al. |
| 5,552,223 A | 9/1996 | Mikami et al. |
| 5,559,264 A | 9/1996 | Bowman et al. |
| 5,616,762 A | 4/1997 | Kropfgans et al. |
| 5,646,326 A | 7/1997 | Schuler |
| 6,015,920 A | 1/2000 | Schilling et al. |
| 6,177,585 B1 | 1/2001 | Chen et al. |
| 6,191,297 B1 | 2/2001 | Batz-Sohn et al. |
| 6,242,630 B1 | 6/2001 | Bade et al. |
| 6,307,082 B1 | 10/2001 | Klein et al. |
| 2001/0044551 A1 | 11/2001 | Childress et al. |
| 2002/0072632 A1 | 6/2002 | Guram et al. |

FOREIGN PATENT DOCUMENTS

| | | |
|---|---|---|
| EP | 0669338 | 2/1995 |
| JP | 4225170 | 7/1992 |
| JP | 4330102 | 11/1992 |
| JP | 6157555 | 6/1994 |
| JP | 8261232 | 9/1996 |
| JP | 11199588 | 7/1999 |

OTHER PUBLICATIONS

Belyakova et al., Patterns of Behavior . . . Zok 44, 2339 (1974) English Translation.
Collman et al., Principles and Applications . . . , (1987), University Science Books pp. 158–164.
Deschler et al., 3–Chloropropyltrialkoxysilanes–Key Intermediates . . . , Agnew Chem. Int. Ed. Engl. 25 (1986) 236–252.
Gulinski, Jacek et al., Synthesis of 3–3–Chloropropyltrialkoxysilanes, Polish Journal of Chem. Tech. 1999, 1, 11–15.
Kolehmainen, E. et al., et al., Mono–, Bi–, and Polynuclear Complexes . . . , J. of Organometallic Chem. 485 (1995) 109–114.
Kono, et al., The Formation of Silylrhodium Complexes . . . , Chem. Soc. of Japan, Chem. Letters, 1975, pp. 189–190.
Lemke, Federick R., et al., RUC12 (PPh3)3 and hydrosilanes, English Science Abstract, Am. Chem. Soc. (2001). 221 NOR–334.
Marciniec, B., et al., Ruthenium Phosphine Complexes . . . , J of Molecular Catalysis, 10 (1981) 123–126.
Marciniec, B., et al., et al., Catalysis of Hydrosilylation . . . , J. of Organometallic Chem. 253 (1983) 349–362.
Ryan, John W., et al., The addition of Silicon Hydrides . . . , J. of Am. Chem. Soc., 1960, 82, 3601.
Svodba, M. et al., Catalysis by metal complexes . . . , Collection Czechoslov. Chem. Commun. vol. 39, 1973, p1235.
Tanaka et al., Ruthenium Complex–catalyzed hydrosilation . . . , J of Molecular Catalysis, 81 1993, 207–214.
Zavin, B.G., et al., Reaction of Ally Halides with . . . , Russian Journal of Gen. Chem., vol. 64, No. 4 Part 2 1994, p. 568.

*Primary Examiner*—Samuel Barts

(57) ABSTRACT

A haloorganoalkoxysilane is prepared by reacting an olefinic halide with an alkoxysilane in which the alkoxy group(s) contain at least two carbon atoms in a reaction medium to which has been added a catalytically effective amount of ruthenium-containing catalyst and a reaction-promoting effective amount of an electron-donating aromatic compound promoter. The process can be used to prepare, inter alia, chloropropyltriethoxysilane, which is a key intermediate in the manufacture of silane coupling agents.

27 Claims, No Drawings

PROCESS FOR MAKING HALOORGANOALKOXYSILANES

BACKGROUND OF THE INVENTION

1. Field of the Invention

This invention relates to a process for making certain haloorganosilicon compounds. More particularly, the invention relates to a process for the preparation of haloorganoalkoxysilane such as chloropropyltrimethoxysilane.

2. Description of the Related Art

Chloropropyltrimethoxysilane is a key intermediate for the preparation of a variety of amino-, mercapto- and methacryloyloxyorganosilanes which are used as silane coupling agents. Chloropropyltrimethoxysilane can also be converted into chloropropyltriethoxysilane, a key intermediate for the preparation of poylsulfane-containing organoalkoxysilanes which are used in the manufacture of silica-filled tires.

U.S. Pat. No. 6,191,297 describes a two step process involving the ethanol esterification of the product obtained from the platinum-catalyzed hydrosilation reaction of trichlorosilane and allyl chloride. This process is highly material- and plant-intensive due to low yields and significant byproduct formation, i.e., propyltrichlorosilane.

A potentially more economical route is the direct hydrosilation reaction of triethoxysilane and allyl chloride. Platinum is the most widely used hydrosilation catalyst and its use for the hydrosilation reaction of allyl chloride and triethoxysilane has been reported. According to U.S. Pat. No. 3,795,656, a 70% yield was obtained for the Pt-catalyzed hydrosilation reaction of allyl chloride and triethoxysilane. Belyakova et al., *Obshch. Khim* 1974, 44, 2439–2442, describes the Pt-catalyzed hydrosilation reaction of silanes with allyl chloride and reports a 14% yield for chloropropyltriethoxysilane. As disclosed in Japanese Patent No. 11,199,588, the Pt-catalyzed hydrosilation reaction of trimethoxysilane and allyl chloride resulted in a 70% yield of chloropropyltrimethoxysilane.

The primary limitation with the hydrosilation reaction of allyl chloride and a silane is a competing elimination reaction. With platinum, the competing elimination reaction is more prevalent with alkoxysilanes than with chlorosilanes. Rhodium and palladium afford primarily elimination products.

Iridium has been reported to be a very efficient catalyst for the hydrosilation reaction of allyl chloride and triethoxysilane. According to U.S. Pat. No. 5,616,762, the iridium-catalyzed hydrosilation reaction of triethoxysilane and allyl chloride is said to be very selective for chloropropyltriethoxysilane with minimal byproducts. Japanese Patent Appl. 4 [1992]-225170 reports similar results for the iridium-catalyzed hydrosilation reaction of allyl chloride and trimethoxysilane. In U.S. Pat. No. 4,658,050, the iridium-catalyzed hydrosilation reaction of alkoxysilanes and allyl chloride utilizes olefin iridium complexes.

Ruthenium has been reported to be a very efficient catalyst for the hydrosilation reaction of allyl chloride and trimethoxysilane. Japanese Patent No. 2,976,011 discloses the Ru-catalyzed hydrosilation reaction of triethoxysilane and allyl chloride to give chloropropyltriethoxysilane in about 41% yield. U.S. Pat. No. 5,559,264 describes the hydrosilation reaction of a methoxysilane and allyl chloride in the presence of a ruthenium catalyst and preferably in the substantial absence of solvent to provide a chloroalkylalkoxysilane. Tanaka et al., *J. Mol. Catal.* 1993, 81, 207–214 report the ruthenium carbonyl-catalyzed hydrosilation reaction of trimethoxysilane and allyl chloride and Japanese Patent Application No. 8[1996]-261232 describes the activation of ruthenium carbonyl for use as a hydrosilation catalyst for the same reaction.

SUMMARY OF THE INVENTION

In accordance with the present invention, a process is provided for preparing a haloorganoalkoxysilane of the general formula:

$$(R^1)_x(R^2O)_{3-x}SiCH_2CHR^3CR^4R^5X$$

wherein $R^1$ is an alkyl of from 1 to 6 carbon atoms, $R^2$ is an alkyl of from 1 to 6 carbon atoms, $R^3$ is an alkyl group of 1 to 6 carbon atoms or hydrogen, $R^4$ is an alkyl of from 1 to 6 carbon atoms, hydrogen or halogen, $R^5$ is hydrogen or an alkyl of from 1 to 6 carbon atoms, X is a halogen and x is 0, 1 or 2, which comprises reacting an olefinic halide of the general formula:

$$H_2C=CR^3CR^4R^5X$$

wherein $R^3$, $R^4$, $R^5$ and X have the aforestated meanings, with a molar excess of alkoxysilane of the general formula:

$$(R^1)_x(R^2O)_{3-x}SiH$$

wherein $R^1$, $R^2$ and x have the aforestated meanings, in a reaction medium to which has been added a catalytically effective amount of ruthenium-containing catalyst and a reaction-promoting effective amount of an electron-donating aromatic compound. The aromatic compound can contain electron-donating groups in order to promote the reaction. In addition, the aromatic compound must be present in a sufficient amount that will promote the reaction and yet not in an amount that will inhibit the reaction. Furthermore, the aromatic compound should be present simultaneously with the ruthenium catalyst either in the aforementioned alkoxysilane or in a catalyst solution.

The foregoing reaction of olefinic halide and alkoxysilane in the presence of a ruthenium catalyst and aromatic compound promoter to provide a haloorganoalkoxysilane can be considered to proceed in accordance with the reaction:

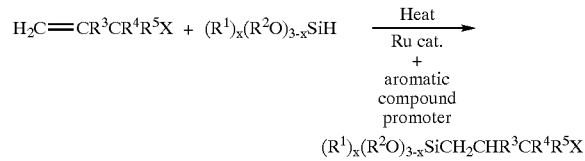

wherein $R^1$, $R^2$, $R^3$, $R^4$, $R^5$, X and x have the meanings stated above.

The process herein can be performed in a variety of commercially available equipment now used for hydrosilation reactions, including equipment in which such reactions are performed in continuous fashion.

By integrating the present process with, e.g., a source of trimethoxysilane, prepared directly from silicon metal and methanol, one can avoid the use of corrosive and hazardous hydrochlorosilanes and eliminate the generation of large amounts of chlorine-containing waste byproducts which are inherent to the use of products derived from hydrochlorosilanes.

DETAILED DESCRIPTION OF THE INVENTION

It has been found that several factors are important for obtaining high yields of haloorganoalkoxysilanes from a one-step hydrosilation reaction between an olefinic halide and an alkoxy silane. First, when all reactants are combined at the start in a batch reaction, selectivity to the desired haloorganoalkoxysilane is highest at lower temperatures and lower reaction rates. Second, when temperature is increased to improve reaction rates, selectivity can be maintained by limiting the concentration of olefinic halide in the reaction mixture. Third, most inert solvents, and particularly aromatic solvents, when employed at the relatively high levels that are typical for reaction solvents may have deleterious effect on rates, selectivities, or both, particularly in a batch system.

Preferably, the process is carried out by slowly adding the olefinic halide to a reaction medium containing the alkoxysilane and reacting them in the presence of a ruthenium metal-containing catalyst and an electron-donating aromatic compound as promotor in either a semi-batch or continuous process. This order of addition effectively maintains a minimum concentration of unreacted olefinic halide in the reaction medium relative to the alkoxysilane, and thus effectively establishes a very large molar excess of the alkoxysilane relative to the olefinic halide in the reaction medium. In general practice, the maximum rate of addition of the olefinic halide to the alkoxysilane will be determined by the reaction rate, which is dependent in part on the reaction temperature, the catalyst concentration, the concentration of electron-donating aromatic compound promoter and by the heat transfer limitations of the reaction equipment, whether a small laboratory reactor or a very large commercial reactor is used, as will be understood by one skilled in the art.

The preferred order of combination can be achieved in semi-batch or continuous operation. In semi-batch operation, a reactor is first charged with a large portion of, and preferably with the full complement of, the molar excess of alkoxysilane. The aromatic compound and ruthenium catalyst can then be added to the alkoxysilane and then reacted with the olefinic halide. Alternatively, the olefinic halide is slowly added to a reactor containing a molar excess of alkoxysilane and the alkoxysilane and olefinic halide are reacted in the presence of a solution of the ruthenium catalyst and aromatic promoter. As used herein, slow addition of olefinic halide generally means at a rate below about 3 moles of olefinic halide per hour per mole of alkoxysilane, and preferably at or below 1 mole per hour per mole of alkoxysilane. For example, in a semi-batch process, an addition rate of 2 moles of olefinic halide/hr/mole of alkoxysilane is practiced when 1 mole of olefinic halide is added to a reactor containing 2 moles of alkoxysilane in 15 minutes. Once the olefinic halide has been added to the reactor, the reaction is continued until complete conversion of the olefinic halide is obtained. While this, in large part, is a function of temperature, catalyst and aromatic promoter concentration, complete conversion generally can be achieved in 1 to 15 hours and more usually between 1 to 10 hours. Completion of the reaction in 1 to 5 hours is not unusual. Some portion of the alkoxysilane can also be added in admixture with the olefinic halide or simultaneously with the addition of the olefinic halide as a separate stream.

In continuous operation, the reactor typically is charged with separate streams of the olefinic halide and alkoxysilane at a mole ratio of alkoxysilane to olefinic halide of from about 1.3 to about 3.0, and preferably at a mole ratio of from about 1.8 to about 2.3. Such operation ensures a proper excess of alkoxysilane in the reaction vessel under steady state operating conditions. For the preferred alkoxysilane, methoxysilane, and preferred olefinic halide, allylic chloride, the preferred mole ratio is from about 1.6 to about 2.3. In continuous operation, the aromatic promoter and the ruthenium catalyst can be added to the olefinic halide and alkoxysilane separately or preferably as a catalyst solution to the reactor in which the aforementioned separate streams of olefinic halide and alkoxysilane are being charged.

The aromatic promoter employed in the process of this invention must be present in the reaction medium in a reaction-promoting amount, i.e., an amount which is below that which inhibits the reaction (as manifested by higher product purities and/or lowered production of byproducts such as organoalkoxysilanes and haloalkoxysilanes) but which increases the yield of the reaction. In general, an effective amount of aromatic promoter can range from about 1 to about 100 mole equivalents per mole of ruthenium metal and preferably from about 5 to about 50 mole equivalents per mole of ruthenium metal and more preferably from about 20 to about 30 mole equivalents per mole of ruthenium metal.

Other hydrosilation reaction conditions, such as temperature, mole ratios of reactants, pressure, time, and catalyst concentration, are not narrowly critical. One has a wide latitude in adjusting these factors to use various pieces of production equipment economically and safely. Such equipment will typically have provisions for heating, cooling, agitation, maintenance of inert atmospheres and purification, as by filtration or distillation. Thus, equipment typically used in the prior art for large scale commercial hydrosilation reactions can be used for the process of the present invention, including equipment wherein olefinic halide is added to a refluxing, condensable stream of hydrosilicon compound in a zone containing a heterogeneous supported hydrosilation catalyst and an electron-donating aromatic promoter.

Reaction conditions can include a reaction temperature of from about 50° to about 130° C. with from about 60° to about 80° C. being preferred. Generally, the process is performed at a pressure at or above atmospheric pressure with atmospheric pressure being preferred. It is recognized that the process of the present invention may provide a high yield of the desired chloroalkylalkoxysilane in a truly batch system; however, a batch reaction will typically be conducted at a lower temperature with consequently longer reaction times. Thus, it is preferred to perform the hydrosilation at an elevated temperature by adding the olefinic halide to a molar excess of the alkoxysilane in the presence of the ruthenium metal-containing catalyst and an aromatic promoter. One particular preferred mode of operation (semi-batch) involves slowly adding the full complement of olefinic halide over a period of time, to obtain a rate of addition of less than 3 moles of olefinic halide per hour per mole of alkoxysilane, to a reactor containing the full complement of the alkoxysilane, for example, from about 1.6 to about 2.3 molar equivalents of trimethoxysilane relative to the full amount of allyl halide to be added. Preferably, the reactor contains 5 to 50 parts per million of ruthenium as $RuCl_3$ hydrate by weight of total reactants and a reaction-promoting effective amount of aromatic promoter and the reaction is conducted at from about 50° to about 130° C. and preferably from about 60° to about 80° C. Excess alkoxysilane, ruthenium catalyst and the aromatic promoter can be recycled effectively to the next batch.

Since the process of the present invention is nearly quantitative with respect to the conversion of olefinic halide to the desired haloorganoalkoxysilane product, particularly in the reaction of allyl chloride with trimethoxysilane to provide chloropropyl-trimethoxysilane, the generation of undesired byproducts is greatly lowered. This reduces the amounts of materials to be destroyed or discarded as waste, to be isolated as separate streams, as by distillation, or to be vented from the reaction system. Since the process of the present invention is highly exothermic, external heating is not normally necessary and reaction times are correspondingly shorter. Generally, the only impurities in significant amounts that need to be removed from the reaction product are the small excess of unreacted alkoxysilane, residual catalyst and aromatic promoter. These may be recycled to the next batch without purification. The low level of residual halide that may be present in the product can be neutralized by methods well known in the art. Where the hydrosilation product of the present invention is used as an intermediate for the production of other organofunctional silicon compounds, its purity on initial synthesis may be sufficient that further purification, such as by distillation, may not be needed.

When applied, e.g., to the preparation of chloropropyltrimethoxysilane, the process of the present invention provides a higher yield of this product, calculated on a molar basis from the limiting reactant, than any one-step or two-step process described in the prior art. This is done through the addition to a reaction medium of an effective amount of an aromatic promoter and an effective amount of the ruthenium catalyst. The process also obtains such yields using significantly lower levels of ruthenium metal-containing catalyst than any process described in the art. In addition, the process of this invention employs an effective amount of electron-donating aromatic compound which facilitates significant increases in product and minimizes wastes. The process also provides a higher yield per unit volume of equipment used, since use of inert solvents is obviated and significant quantities of waste by-products are not generated. The preferred order of combination of reactants in the present invention is in fact opposite to that employed to maximize the yield of chloropropyltrichlorosilane from one reported platinum-catalyzed reaction of trichlorosilane with allyl chloride. Moreover, the obtained yield is significantly higher than that reported for the platinum-catalyzed reaction of triethylsilane with allyl chloride, which is maximized by the addition of allyl chloride, necessarily containing trichlorosilane as a hydrosilation promoter, to the triethylsilane.

While the process of the present invention does not require operation at a pressure above atmospheric pressure, an elevated pressure may be used, for example up to two atmospheres pressure, to control inadvertent potential emissions of allyl halide to the environment by using a closed reactor. A pressure below atmospheric pressure may be used if a reaction temperature below the atmospheric pressure boiling point of the alkoxysilane is desired.

Olefinic halides which are suitable for use herein include allyl chloride, methallyl chloride, 3-chloro-1-butene, 3,4-dichloro-1-butene, 2-chloropropene, and the like. Of these, allyl chloride, $CH_2=CH_2CH_2Cl$, is preferred.

Alkoxysilanes that are suitable for use in the present invention include trimethoxysilane, methyldimethoxysilane, dimethylmethoxysilane, triethoxysilane, methyldiethoxysilane, dimethylethoxysilane, ethyldiethoxysilane, diethylethoxysilane, and the like. Of these alkoxysilanes, the ethoxysilanes are preferred with triethoxysilane being more preferred.

The ruthenium metal-containing catalyst and the aromatic promoter must be present in the reaction medium and can be added in solution with the alkoxysilane, or with the olefinic halide, or both may be present in heterogeneous form in a catalytic zone to which the reactants are introduced. A variety of homogeneous and heterogeneous forms of ruthenium metal-containing compounds can be used as catalysts, and use levels (based on contained metal) can be as low as those of commercially practiced platinum-catalyzed hydrosilation reactions. For example, ruthenium concentrations between about 2 and 300 ppm are generally suitable.

If oxygen is needed for catalyst activation, the amount of oxygen normally present in commercial raw materials, especially the reactants themselves, should generally be sufficient. This is particularly true for ruthenium carbonyl catalysts. If further catalyst activation is necessary, such can be accomplished simply by adding dilute oxygen, as for example, a mixture of 3% $O_2$ in $N_2$, to one or more of the reactants, or to the reaction medium to elevate the oxygen level encountered by the catalyst. Separate activation may more likely be required when the catalysts are ruthenium-phosphine complexes.

Suitable ruthenium-metal containing catalysts can be selected from homogeneous and heterogeneous ruthenium metal-containing compounds and complexes including the following: $Ru_3(CO)_{12}$, $[Ru(CO)_3Cl_2]_2$; cyclooctadiene-$RuCl_2$; $RuCl_3$, $(Ph_3P)_2Ru(CO)_2Cl_2$; $(Ph_3P)_3Ru(CO)H_2$; Ru on Fe; Ru on $Al_2O_3$; Ru on carbon; $Ru(AcAc)_3$; $RuBr_3$ and the like where Ph is a phenyl group and AcAc is an acetylacetonate group.

Ruthenium metal-containing compounds constituting ruthenium complexes containing only triphenylphosphine, hydrogen and chlorine ligands such as $(Ph_3P)_3RuCl_2$, $(Ph_3P)_3RuHCl$ and $(Ph_3P)_3RuH_2$ are ineffective as catalysts for the reaction of trimethoxysilane with olefinic halide in the presence or absence of oxygen. This lack of catalytic activity is consistent with the results of prior investigators who examined the hydrosilation of allyl chloride with triethoxysilane. Where phosphine ligands are present, ligands other than or in addition to hydrogen or chlorine, e.g., carbonyl and olefin ligands, should also be present and a slightly higher level of activating oxygen may be needed. Although ruthenium complexes containing an aromatic compound such as, for example, (π-arene) ruthenium complexes along with at least one mole equivalent of the aromatic compound vs. ruthenium metal are also suitable. Examples of (π-arene) ruthenium complexes are (p-cymene) ruthenium (II) chloride dimer or (benzene) ruthenium (II) chloride dimer.

The preferred ruthenium catalysts are the ruthenium chloride compounds, with $RuCl_3$ hydrate being the most preferred. Catalyst from one batch can be recycled to the next batch without significant loss of activity. Catalyst use level may be in the range of 1.0 to 300 parts per million of contained Ru metal based on the total reactant charge, with 5 to 50 parts per million being preferred.

Suitable aromatic compounds include, for example, benzene, ethylbenzene, diethylbenzene, triethylbenzene, n-butylbenzene, di-t-butylbenzene, bibenzyl, toluene, t-butyltoluene, anisole, 1-phenylhexane, 1-phenyldodecane, Nalkylene® (a mixture of n-alkylbenzene of from $C_8$ to $C_{12}$), Therminol® (a mixture of ethylbenzene and bibenzyl isomers), m-xylene, mesitylene, p-cymene, diphenylmethane, triphenylmethane, phenyl ether, phenothiazine, and biphenyl, and they can be present in an amount from about 1 to about 100 mole equivalents vs. moles of ruthenium metal and preferably from about 5 to about 50 mole equivalents vs. moles of ruthenium metal and more preferably from about 20 to about 30 mole equivalents vs. moles of ruthenium metal.

The haloorganoalkoxysilane product of the process of the present invention may be purified by standard means, as by distillation, or where used as intermediates for a subsequent preparation, may be used directly without intermediate purification.

As noted above, the reaction also can be conducted in a continuous fashion by adding the alkoxysilane and olefinic halide reactants to the reactor at the desired molar excess of the silane. At steady state, the reactor will contain a sufficient excess of the alkoxysilane in admixture with product haloorganoalkoxysilane to allow substantially quantitative yield of the desired product. The excess alkoxysilane can conveniently be recovered from the product stream and recycled.

Whereas the exact scope of the present invention is set forth in the appended claims, the following specific examples illustrate certain aspects of the present invention and, more particularly, point out the various aspects of the method for evaluating the same. However, the examples are set forth for illustrative purposes only and are not to be construed as limitations on the present invention. The abbreviations g, ppm, equiv., GC and TMS respectively represent grams, parts per million, molar equivalent, gas chromatography and trimethoxysilane. Temperature is given in degrees centigrade. Yield percentages are determined by GC using an internal standard, except where yields are determined by actual weight, following vacuum distillation of the product. Unless stated otherwise, all reactions were run in standard laboratory glassware at atmospheric pressure under an inert atmosphere of nitrogen. In each example, product structures were identified by GC, GC/mass spectrometry, infrared spectroscopy, or nuclear magnetic resonance.

All of the reactions in the following examples were carried out under a nitrogen atmosphere. Allyl chloride, methallyl chloride, trimethoxysilane, and RuCl$_3$ hydrate were used without further purification. TMS was distilled using a 5 tray Oldershaw column under atmospheric pressure and stored in either a glass or stainless steel bottle. Typical TMS purity was ~98% (wt/wt). All GC data is expressed in weight mass % (wt/wt) and was normalized for excess TMS.

The following abbreviations and tradenames (with their descriptions) appear in the examples:

| Abbreviation | Description |
| --- | --- |
| TMS | trimethoxysilane |
| Cl-TMOS | chlorotrimethoxysilane |
| TMOS | tetramethoxysilane |
| Propyl-TMS | n-propyltrimethoxysilane |
| Cl-CPTMS | 3-chloropropylchlorodimethoxysilane |
| CPTMS | 3-chloropropyltrimethoxysilane |
| Bis TMS Propane | bis(trimethoxysilyl)propane |
| Isobutyl-TMS | isobutyltrimethoxysilane |
| Cl-CIBTMS | 3-chloroisobutylchlorodimethoxysilane |
| CIBTMS | 3-chloroisobutyltrimethoxysilane |
| Bis TMS Isobutane | bis(trimethoxysilyl)isobutane |
| Nalkylene ® | A mixture of n-alkylbenzenes consisting of C$_8$ to C$_{12}$. |
| Therminol ® | A mixture of ethylbenzene, bibenzyl and related isomers. |

EXAMPLE 1

At ambient temperature, 29.02 g of trimethoxysilane (0.2351 moles) was treated with 0.016 g of toluene, and 0.025 g of a 3.85% Ru (wt/wt) methanol solution of Ruthenium (III) chloride hydrate (24 ppm Ru). This trimethoxysilane solution was warmed, and at 80° C. it was treated with 11.2 g of allyl chloride (0.1449 moles). The allyl chloride was added over one hour while maintaining the trimethoxysilane solution between 78–83° C. After this addition was completed, the reaction was maintained at 80° C. for one hour. After this time, the solution was analyzed with GC. The GC data for this reaction was:

| Allyl chloride | Propyl chloride | Cl-TMOS | TMOS | Propyl-TMS | Cl-CPTMS | CPTMS |
| --- | --- | --- | --- | --- | --- | --- |
| 0.095 | 0.107 | 0.121 | 2.850 | 1.846 | 0.164 | 92.529 |

EXAMPLE 2

At ambient temperature, 28.91 g of trimethoxysilane (0.2342 moles) was treated with 0.056 g of toluene, and 0.025 g of a 3.85% Ru (wt/wt) methanol solution of Ruthenium (III) chloride hydrate (24 ppm Ru). This trimethoxysilane solution was warmed, and at 80° C. it was treated with 11.2 g of allyl chloride (0.1449 moles). The allyl chloride was added over one hour while maintaining the trimethoxysilane solution between 78–83° C. After this addition was completed, the reaction was maintained at 80° C. for one hour. After this time, the solution was analyzed with GC. The GC data for this reaction was:

| Allyl chloride | Propyl chloride | Cl-TMOS | TMOS | Propyl-TMS | Cl-CPTMS | CPTMS |
| --- | --- | --- | --- | --- | --- | --- |
| 0.001 | 0.088 | 1.267 | 3.242 | 1.498 | 0.340 | 88.904 |

EXAMPLE 3

At ambient temperature, 28.91 g of trimethoxysilane (0.2342 moles) was treated with 0.64 g of toluene, and 0.050 g of a 3.85% Ru (wt/wt) methanol solution of Ruthenium (III) chloride hydrate (47 ppm Ru). This trimethoxysilane solution was warmed and at 80° C., it was treated with 11.2 g of allyl chloride (0.1449 moles). The allyl chloride was added over one hour while maintaining the trimethoxysilane solution between 78–83° C. After this addition was completed, the reaction was maintained at 80° C. for one hour. After this time, the solution was analyzed with GC. The GC data for this reaction was:

| Allyl chloride | Propyl chloride | Cl-TMOS | TMOS | Propyl-TMS | Cl CPTMS | CPTMS | Bis TMS Propane |
|---|---|---|---|---|---|---|---|
| 2.929 | 0.087 | 1.007 | 2.377 | 1.237 | 0.679 | 87.310 | 0.297 |

EXAMPLE 4

At ambient temperature, 28.91 g of trimethoxysilane (0.2342 moles) was treated with 0.64 g of toluene, and 0.050 g of a 3.85% Ru (wt/wt) methanol solution of Ruthenium (III) chloride hydrate (47 ppm Ru). This trimethoxysilane solution was warmed and at 80° C., it was treated with 11.2 g of allyl chloride (0.1449 moles). The allyl chloride was added over one hour while maintaining the trimethoxysilane solution between 78–83° C. After this addition was completed, the reaction was maintained at 80° C. for one hour. After this time, the solution was analyzed with GC. The GC data for this reaction was:

| Allyl chloride | Propyl chloride | Cl-TMOS | TMOS | Propyl-TMS | Cl-CPTMS | CPTMS |
|---|---|---|---|---|---|---|
| 18.461 | 0.449 | 1.619 | 3.691 | 0.340 | 0.546 | 66.719 |

EXAMPLE 5

At ambient temperature, 28.67 g of trimethoxysilane (0.2323 moles) was treated with 0.016 g of Therminol® 59, and 0.020 g of a 3.85% Ru (wt/wt) methanol solution of Ruthenium (III) chloride hydrate (19 ppm Ru). This trimethoxysilane solution was warmed, and at 78° C. it was treated with 11.2 g of allyl chloride (0.1449 moles). The allyl chloride was added over one hour while maintaining the trimethoxysilane solution between 78–83° C. After this addition was completed, the reaction was maintained at 80° C. for one hour. After this time, the solution was analyzed with GC. The GC data for this reaction was:

| Allyl chloride | Propyl chloride | Cl-TMOS | TMOS | Propyl-TMS | Cl-CPTMS | CPTMS | Bis TMS Propane |
|---|---|---|---|---|---|---|---|
| 0.041 | 0.075 | 0.970 | 1.693 | 1.055 | 0.123 | 93.675 | 0.155 |

EXAMPLE 6

At ambient temperature, 150.34 g of trimethoxysilane (1.2203 moles) was treated with 0.280 g of ethylbenzene, and 0.080 g of 3.85% Ru (wt/wt) methanol solution of ruthenium(III) chloride hydrate (23 ppm Ru). This trimethoxysilane solution was warmed, and at 80° C. it was treated with 59.56 g of allyl chloride (0.7705 moles). The allyl chloride was added over one hour while maintaining the trimethoxysilane solution between 80–81° C. After this addition was completed, the reaction was maintained at 80° C. for one hour. After this time, the solution was analyzed with GC. The GC data for this reaction was:

| Allyl chloride | Propyl chloride | Cl-TMOS | TMOS | Propyl-TMS | Cl-CPTMS | CPTMS | Bis TMS Propane |
|---|---|---|---|---|---|---|---|
| 0.135 | 0.115 | 0.837 | 1.896 | 1.167 | 0.206 | 90.320 | 0.115 |

EXAMPLE 7

At ambient temperature, 160.78 g of trimethoxysilane (1.3056 moles) was treated with 0.140 g of n-butylbenzene, and 0.080 g of 3.85% Ru (wt/wt) methanol solution of ruthenium(III) chloride hydrate (22 ppm Ru). This trimethoxysilane solution was warmed, and at 80° C. it was treated with 63.72 g of allyl chloride (0.8243 moles). The allyl chloride was added over one hour while maintaining the trimethoxysilane solution between 80–81° C. After this addition was completed, the reaction was maintained at 80° C. for one hour. After this time, the solution was analyzed with GC. The GC data for this reaction was:

| Allyl chloride | Propyl chloride | Cl-TMOS | TMOS | Propyl-TMS | Cl-CPTMS | CPTMS | Bis TMS Propane |
|---|---|---|---|---|---|---|---|
| 0.051 | 0.155 | 0.942 | 1.859 | 1.314 | 0.284 | 91.918 | 0.395 |

EXAMPLE 8

At ambient temperature, 161.96 g of trimethoxysilane (1.3147 moles) was treated with 0.110 g of anisole, and 0.080 g of 3.85% Ru (wt/wt) methanol solution of ruthenium (III) chloride hydrate (22 ppm Ru). This trimethoxysilane solution was warmed, and at 80° C. it was treated with 64.17 g of allyl chloride (0.8301 moles). The allyl chloride was added over one hour while maintaining the trimethoxysilane solution between 80–81° C. After this addition was completed, the reaction was maintained at 80° C. for one hour. After this time, the solution was analyzed with GC. The GC data for this reaction was:

| Allyl chloride | Propyl chloride | Cl-TMOS | TMOS | Propyl-TMS | Cl-CPTMS | CPTMS | Bis TMS Propane |
|---|---|---|---|---|---|---|---|
| 0.001 | 0.223 | 1.019 | 2.245 | 1.460 | 0.379 | 91.213 | 0.472 |

EXAMPLE 9

At ambient temperature, 165.22 g of trimethoxysilane (1.3413 moles) was treated with 0.170 g of diphenylmethane, and 0.080 g of 3.85% Ru (wt/wt) methanol solution of ruthenium(III) chloride hydrate (22 ppm Ru). This trimethoxysilane solution was warmed, and at 80° C. it was treated with 65.47 g of allyl chloride (0.8469 moles). The allyl chloride was added over one hour while maintaining the trimethoxysilane solution between 80–81° C. After this addition was completed, the reaction was maintained at 80° C. for one hour. After this time, the solution was analyzed with GC. The GC data for this reaction was:

| Allyl chloride | Propyl chloride | Cl-TMOS | TMOS | Propyl-TMS | Cl-CPTMS | CPTMS | Bis TMS Propane |
|---|---|---|---|---|---|---|---|
| 0.001 | 0.178 | 0.947 | 1.898 | 1.318 | 0.257 | 92.112 | 0.386 |

EXAMPLE 10

At ambient temperature, 28.34 g of trimethoxysilane (0.2296 moles) was treated with 0.024 g of bibenzyl, and 0.020 g of a 3.85% Ru (wt/wt) as a methanol solution of ruthenium (III) chloride hydrate solution. This trimethoxysilane solution was warmed, and at 78° C. it was treated with 11.2 g of allyl chloride (0.1449 moles). The allyl chloride was added over one hour while maintaining the trimethoxysilane solution between 78–83° C. After this addition was completed, the reaction was maintained at 80° C. for one hour. After this time, the solution was analyzed with GC. The GC data for this reaction was:

| Allyl chloride | Propyl chloride | Cl-TMOS | TMOS | Propyl-TMS | Cl-CPTMS | CPTMS | Bis TMS Propane |
|---|---|---|---|---|---|---|---|
| 0.029 | 0.127 | 0.768 | 1.616 | 1.064 | 0.287 | 93.399 | 0.197 |

EXAMPLE 11

At ambient temperature, 165.22 g of trimethoxysilane (1.3416 moles) was treated with 0.250 g of triphenylmethane, and 0.080 g of 3.85% Ru (wt/wt) methanol solution of ruthenium(III) chloride hydrate (22 ppm Ru). This trimethoxysilane solution was warmed, and at 80° C. it was treated with 65.48 g of allyl chloride (0.8470 moles). The allyl chloride was added over one hour while maintaining the trimethoxysilane solution between 80–81° C. After this addition was completed, the reaction was maintained at 80° C. for one hour. After this time, the solution was analyzed with GC. The GC data for this reaction was:

| Allyl chloride | Propyl chloride | Cl-TMOS | TMOS | Propyl-TMS | Cl-CPTMS | CPTMS | Bis TMS Propane |
|---|---|---|---|---|---|---|---|
| 0.012 | 0.168 | 1.222 | 2.069 | 1.890 | 0.535 | 90.319 | 0.487 |

EXAMPLE 12

At ambient temperature, 28.61 g of trimethoxysilane (0.2318 moles) was treated with 0.024 g of bibenzyl, and 0.020 g of a 3.85% Ru (wt/wt) as a methanol solution of ruthenium (III) chloride hydrate solution. This trimethoxysilane solution was warmed, and at 60° C. it was treated with 11.2 g of allyl chloride (0.1449 moles). The allyl chloride was added over one hour while maintaining the trimethoxysilane solution between 60–63° C. After this addition was completed, the reaction was maintained at 60° C. for one hour. After this time, the solution was analyzed with GC. The GC data for this reaction was:

| Allyl chloride | Propyl chloride | Cl-TMOS | TMOS | Propyl-TMS | Cl-CPTMS | CPTMS | Bis TMS Propane |
|---|---|---|---|---|---|---|---|
| 11.943 | 0.409 | 0.842 | 2.708 | 0.787 | 0.657 | 79.287 | 0.276 |

EXAMPLE 13

At ambient temperature, 161.16 g of trimethoxysilane (1.3082 moles) was treated with 0.190 g of bibenzyl, and 0.80 g of a 3.85% Ru (wt/wt) as a methanol solution of ruthenium (III) chloride hydrate solution (22 ppm Ru). This trimethoxysilane solution was warmed, and at 70° C. it was treated with 63.85 g of allyl chloride (0.8260 moles). The allyl chloride was added over one hour while maintaining the trimethoxysilane solution between 70–72° C. After this addition was completed, the reaction was maintained at 70° C. for one hour. After this time, the solution was analyzed with GC. The GC data for this reaction was:

| Allyl chloride | Propyl chloride | Cl-TMOS | TMOS | Propyl-TMS | Cl-CPTMS | CPTMS | Bis TMS Propane |
|---|---|---|---|---|---|---|---|
| 0.062 | 0.155 | 0.657 | 1.558 | 0.908 | 0.908 | 93.411 | 0.325 |

EXAMPLE 14

At ambient temperature, 28.41 g of trimethoxysilane (0.2302 moles) was treated with 0.032 g of bibenzyl, and 0.020 g of a 3.85% Ru (wt/wt) as a methanol solution of ruthenium (III) chloride hydrate solution. This trimethoxysilane solution was warmed, and at 78° C. it was treated with 11.2 g of allyl chloride (0.1449 moles). The allyl chloride was added over one hour while maintaining the trimethoxysilane solution between 78–83° C. After this addition was completed, the reaction was maintained at 80° C. for one hour. After this time, the solution was analyzed with GC. The GC data for this reaction was:

| Allyl chloride | Propyl chloride | Cl-TMOS | TMOS | Propyl-TMS | Cl-CPTMS | CPTMS | Bis TMS Propane |
|---|---|---|---|---|---|---|---|
| 0.029 | 0.113 | 0.711 | 1.541 | 0.962 | 0.191 | 93.864 | 0.152 |

EXAMPLE 15

At ambient temperature, 163.03 g of trimethoxysilane (1.3248 moles) was treated with 0.25 g of bibenzyl, and 0.100 g of a 3.85% Ru (wt/wt) as a methanol solution of ruthenium (III) chloride hydrate solution. This trimethoxysilane solution was warmed, and at 95° C. it was treated with 64.66 g of allyl chloride (0.8364 moles). The allyl chloride was added over one hour while maintaining the trimethoxysilane solution between 94–96° C. After this addition was completed, the reaction was maintained at 95° C. for one hour. After this time, the solution was analyzed with GC. The GC data for this reaction was:

| Allyl chloride | Propyl chloride | Cl-TMOS | TMOS | Propyl-TMS | Cl-CPTMS | CPTMS | Bis TMS Propane |
|---|---|---|---|---|---|---|---|
| 0.239 | 0.157 | 1.695 | 2.175 | 2.197 | 0.296 | 88.911 | 0.470 |

EXAMPLE 16

At ambient temperature, 28.32 g of trimethoxysilane (0.2294 moles) was treated with 0.036 g of a 2.23% Ru (wt/wt) dichloromethane solution of (p-cymene)ruthenium (II) chloride dimer. This trimethoxysilane solution was warmed, and at 78° C. it was treated with 11.2 g of allyl chloride (0.1449 moles). The allyl chloride was added over one hour while maintaining the trimethoxysilane solution between 78–83° C. After this addition was completed, the reaction was maintained at 80° C. for one hour. After this time, the solution was analyzed with GC. The GC data for this reaction was:

| Allyl chloride | Propyl chloride | Cl-TMOS | TMOS | Propyl-TMS | Cl-CPTMS | CPTMS | Bis TMS Propane |
|---|---|---|---|---|---|---|---|
| 0.048 | 0.158 | 1.097 | 1.806 | 1.304 | 0.088 | 92.189 | 0.326 |

EXAMPLE 17

At ambient temperature, 160.07 g of trimethoxysilane (1.3008 moles) was treated with a catalyst solution consisting of 0.074 g of toluene, 0.120 g of ruthenium(III) chloride hydrate, and 62 g of methanol (1.7 mole equiv. of toluene vs. Ru). This trimethoxysilane solution was warmed, and at 80° C. it was treated with 63.40 g of allyl chloride (0.8213 moles). The allyl chloride was added over one hour while maintaining the trimethoxysilane solution between 79–82° C. After this addition was completed, the reaction was maintained at 80° C. for one hour. After this time, the solution was analyzed with GC. The GC data for this reaction was:

| Allyl chloride | Propyl chloride | Cl-TMOS | TMOS | Propyl-TMS | Cl-CPTMS | CPTMS | Bis TMS Propane |
|---|---|---|---|---|---|---|---|
| 0.048 | 0.158 | 1.097 | 1.806 | 1.304 | 0.088 | 92.189 | 0.326 |

Catalyst Solutions

Two solutions were prepared by dissolving ruthenium (III) chloride hydrate in methanol and treating this solution with the specified quantity of diphenylmethane at ambient temperature:

|  | Catalyst Solution | |
|---|---|---|
|  | A | B |
| RuCl$_3$ hydrate | 1.034 g | 1.047 g |
| Diphenylmethane | 7.070 g | 3.570 g |
| Methanol | 9.316 g | 9.433 g |
| Mole Ratio of Diphenylmethane vs. Ru | 10:1 | 5:1 |

After mixing, the resulting solutions were ready to be used.

EXAMPLE 18

At ambient temperature, 163.93 g of trimethoxysilane (1.3330 moles) was treated with 0.200 g of the catalyst solution A as prepared above (21 ppm Ru). This trimethoxysilane solution was warmed, and at 80° C. it was treated with 64.89 g of allyl chloride (0.8394 moles). The allyl chloride was added over one hour while maintaining the trimethoxysilane solution between 79–81° C. After this addition was completed, the reaction was maintained at 80° C. for one hour. After this time, the solution was analyzed with GC. The GC data for this reaction was:

| Allyl chloride | Propyl chloride | Cl-TMOS | TMOS | Propyl-TMS | Cl-CPTMS | CPTMS | Bis TMS Propane |
|---|---|---|---|---|---|---|---|
| 0.001 | 0.139 | 0.751 | 1.499 | 1.162 | 0.101 | 93.970 | 0.302 |

EXAMPLE 19

Over the course of eight hours (four turnovers), trimethoxysilane was added a rate of 1.47 g/min, allyl chloride was added a rate of 0.78 g/min and prepared catalyst solution B was added a rate of 0.167 mL/hr using syringe pump to a one liter glass reactor. A constant level was maintained in the stirrer reactor such that the residence time was 2 hours. The reactor was maintained at 75° C. The catalyst loading was ~20 ppm Ru, and the ratio of trimethoxysilane vs. allyl chloride was maintained at ~2.0:1.0. Water condensers were used on the reactor. On startup, the reactor contained ~53% chloro-propyltrimethoxysilane, ~41% trimethoxysilane and ~20 ppm Ru (wt/wt). The crude CPTMS in the reactor based on the average GC wt % and standard deviation for four turnovers in the reactor consisted of

| Allyl chloride | Propyl chloride | TMS | Cl-TMOS | TMOS | Propyl-TMS | Cl-CPTMS | CPTMS | Bis TMS Propane |
|---|---|---|---|---|---|---|---|---|
| 0.033 ± 0.002 | 0.399 ± 0.020 | 41.697 ± 0.891 | 0.518 ± 0.025 | 0.971 ± 0.093 | 0.591 ± 0.042 | 0.155 ± 0.034 | 54.166 ± 0.885 | 0.102 ± 0.023 |

During continuous operation, the material in the reactor was continuously fed to the $2^{nd}$ tray from the top of a 15 tray Oldershaw column. The column reboiler temperature was maintained between 167–169° C. The lites were recycled with the fresh trimethoxysilane back into the reactor at a rate of 1.17 g/min. The composition of the lites based on the average GC data wt % and standard deviation for four reactor turnovers was:

| Allyl chloride | Propyl chloride | TMS | Cl-TMOS | TMOS | Propyl-TMS | Cl-CPTMS | CPTMS | Bis TMS Propane |
|---|---|---|---|---|---|---|---|---|
| 0.053 ± 0.050 | 0.877 ± 0.332 | 97.022 ± 0.374 | 0.081 ± 0.038 | 0.142 ± 0.033 | 0.029 ± 0.020 | 0.012 ± 0.020 | 0.024 ± 0.008 | 0.000 ± 0.000 |

The strip material from the column reboiler unit was continuous fed into a CPTMS reservoir. Over the course of eight hours (4 turnovers), the resulting crude CPTMS was collected at a rate of 2.21 g/min and its composition based on the average GC data wt % and standard deviation for four turnovers was:

| Allyl chloride | Propyl chloride | TMS | Cl-TMOS | TMOS | Propyl-TMS | Cl-CPTMS | CPTMS | Bis TMS Propane |
|---|---|---|---|---|---|---|---|---|
| 0.000 ± 0.000 | 0.000 ± 0.000 | 3.475 ± 0.183 | 0.672 ± 0.086 | 1.526 ± 0.156 | 1.002 ± 0.119 | 0.260 ± 0.159 | 91.309 ± 0.473 | 0.226 ± 0.102 |

EXAMPLE 20

At ambient temperature, 28.48 g of trimethoxysilane (0.2307 moles) was treated with 0.034 g of bibenzyl, and 0.033 g of a 3.85% Ru (wt/wt) methanol solution of ruthenium (III) chloride hydrate (30 ppm Ru). This trimethoxysilane solution was warmed and at 80° C., it was treated with 13.30 g of methallyl chloride (0.1454 moles). The methallyl chloride was added over one hour while maintaining the trimethoxysilane solution between 78–83° C. After this addition was completed, the reaction was maintained at 80° C. for one hour. After this time, the solution was analyzed with GC. The GC data for this reaction was:

| Methallyl chloride | Isobutyl chloride | Cl-TMOS | TMOS | Isobutyl-TMS | Cl-CIBTMS | CIBTMS | Bis TMS isobutane |
|---|---|---|---|---|---|---|---|
| 0.471 | 1.404 | 0.872 | 1.588 | 2.054 | 0.058 | 90.457 | 0.306 |

COMPARATIVE EXAMPLE 1

At ambient temperature, 154.92 g of trimethoxysilane (1.2581 moles) was treated with 0.070 g of a 3.85% Ru (wt/wt) methanol solution of ruthenium (III) chloride hydrate (23 ppm Ru) and warmed. At 80° C., this trimethoxysilane solution was treated with 61.40 g of allyl chloride (0.7943 moles). An exothermic reaction was observed and the trimethoxysilane solution was maintained between 79–81° C. throughout the allyl chloride addition. The allyl chloride was added over the course of one hour using a syringe pump. After this addition was completed, the reaction was maintained at 80° C. for one hour. After this time, the reaction was allowed to cool to ambient temperature and then analyzed. The GC data for this reaction was:

| Allyl chloride | Propyl chloride | Cl-TMOS | TMOS | Propyl-TMS | Cl-CPTMS | CPTMS | Bis TMS Propane |
|---|---|---|---|---|---|---|---|
| 0.026 | 0.388 | 1.600 | 3.784 | 2.599 | 1.266 | 86.249 | 0.833 |

COMPARATIVE EXAMPLE 2

At ambient temperature, 156.57 g of trimethoxysilane (1.2723 moles) was treated with 0.080 g of a 3.85% Ru (wt/wt) methanol solution of ruthenium (III) chloride hydrate (23 ppm Ru) and warmed. At 80° C., this trimethoxysilane solution was treated with 62.10 g of allyl chloride (0.8033 moles). An exothermic reaction was observed and the trimethoxysilane solution was maintained between 79–81° C. throughout the allyl chloride addition. The allyl chloride was added over the course of one hour using a syringe pump. After this addition was completed, the reaction was maintained at 80° C. for one hour. After this time, the reaction was allowed to cool to ambient temperature and then analyzed. The GC data for this reaction was:

| Allyl chloride | Propyl chloride | Cl-TMOS | TMOS | Propyl-TMS | Cl-CPTMS | CPTMS | Bis TMS Propane |
|---|---|---|---|---|---|---|---|
| 0.020 | 0.349 | 1.585 | 3.350 | 2.554 | 1.314 | 86.692 | 1.039 |

COMPARATIVE EXAMPLE 3

Example 3 was conducted the same as comparative example 1 except the allyl chloride used had been purchased from Aldrich Chemical. The GC data for this reaction was:

| Allyl chloride | Propyl chloride | Cl-TMOS | TMOS | Propyl-TMS | Cl-CPTMS | CPTMS | Bis TMS Propane |
|---|---|---|---|---|---|---|---|
| 0.047 | 0.178 | 1.438 | 3.015 | 1.817 | 0.636 | 88.109 | 0.938 |

COMPARATIVE EXAMPLE 4

Example 4 was conducted the same as comparative example 1 except the allyl chloride used had been purchased from Aldrich Chemical. The GC data for this reaction was:

| Allyl chloride | Propyl chloride | Cl-TMOS | TMOS | Propyl-TMS | Cl-CPTMS | CPTMS | Bis TMS Propane |
|---|---|---|---|---|---|---|---|
| 0.047 | 0.160 | 1.083 | 3.040 | 1.611 | 0.505 | 88.734 | 0.526 |

TABLE 1

GC data for evaluation of the Ru-catalyzed hydrosilation of allyl chloride and trimethoxysilane.

| Comparative Example | Aromatic compound | Allyl chloride | Propyl chloride | Cl-TMOS | TMOS | Propyl-TMS | Cl-CPTMS | CPTMS | Bis TMS propane |
|---|---|---|---|---|---|---|---|---|---|
| 1 | Dow Chemical allyl chloride | 0.026 | 0.388 | 1.600 | 3.784 | 2.599 | 1.266 | 86.249 | 0.833 |
| 2 | Dow Chemical allyl chloride | 0.020 | 0.349 | 1.585 | 3.350 | 2.554 | 1.314 | 86.692 | 1.039 |
| 3 | Aldrich Chemical allyl chloride | 0.047 | 0.178 | 1.438 | 3.015 | 1.817 | 0.636 | 88.109 | 0.938 |
| 4 | Aldrich Chemical allyl chloride | 0.047 | 0.160 | 1.083 | 3.040 | 1.611 | 0.505 | 88.734 | 0.526 |
| | Average for Comparative examples 1–4 Standard deviation | 0.035 ± 0.012 | 0.269 ± 0.101 | 1.427 ± 0.208 | 3.297 ± 0.310 | 2.145 ± 0.438 | 0.930 ± 0.363 | 87.446 ± 1.012 | 0.834 ± 0.192 |

All reactions were conducted using a 60% mole excess of TMS vs. allyl chloride, 20–30 ppm Ru (RuCl$_3$ hydrate methanol solution) at 78–83° C. with a one hour addition of allyl chloride followed by one hour at 78–83° C. All GC data was normalized for excess TMS by dividing the GC value of each component by the following value: (100.0-GC value of TMS). All GC data was obtained by SV Chrom lab personnel.

COMPARATIVE EXAMPLE 5

This comparative example was conducted analogous to Example 1 as reported in U.S. Pat. No. 6,015,920 by Schilling Jr. and Bowman. Over the course of eight hours (four turnovers), 1.45 g/min of new trimethoxysilane, 0.78 g/min of allyl chloride and 0.114 mL/hr of a 3.85% Ru (wt/wt) methanol solution of ruthenium(III) chloride solution were added to a one liter glass reactor. A constant level was maintained in the stirred reactor such that the residence time was 2 hours. The reactor was maintained at 75° C. The catalyst loading was ~20 ppm Ru, and the ratio of trimethoxysilane vs. allyl chloride was maintained at ~2.0:1.0. Water condensers were used on the reactor. On startup, the reactor contained ~53% chloropropyltrimethoxysilane, ~41% trimethoxysilane and ~20 ppm Ru (wt/wt). The crude CPTMS in the reactor based on the average GC wt % and standard deviation after four turnovers in the reactor consisted of

| Allyl chloride | Propyl chloride | TMS | Cl-TMOS | TMOS | Propyl-TMS | Cl-CPTMS | CPTMS | Bis TMS Propane |
|---|---|---|---|---|---|---|---|---|
| 0.014 ± 0.014 | 0.438 ± 0.032 | 40.717 ± 1.992 | 0.825 ± 0.065 | 1.656 ± 0.307 | 0.975 ± 0.071 | 0.417 ± 0.030 | 52.880 ± 1.924 | 0.406 ± 0.070 |

During continuous operation, the material in the reactor was continuously fed to the $2^{nd}$ tray from the top of a 15 tray Oldershaw column. The column reboiler temperature was maintained between 167–169° C. The lites were recycled with the fresh trimethoxysilane back into the reactor at a rate of 1.16 g/min. The composition of the lites based on the average GC data wt % and standard deviation for four reactor turnovers was:

| Allyl chloride | Propyl chloride | TMS | Cl-TMOS | TMOS | Propyl-TMS | Cl-CPTMS | CPTMS | Bis TMS Propane |
|---|---|---|---|---|---|---|---|---|
| 0.187 ± 0.133 | 1.449 ± 0.345 | 96.290 ± 0.348 | 0.119 ± 0.054 | 0.236 ± 0.049 | 0.043 ± 0.010 | 0.000 ± 0.000 | 0.177 ± 0.031 | 0.000 ± 0.000 |

The strip material from the column reboiler unit was continuous fed into a CPTMS reservoir. Over the course of eight hours (4 turnovers), the crude CPTMS was collected at a rate of 2.21 g/min and its composition based on the average GC data wt % and standard deviation for four turnovers was:

| Allyl chloride | Propyl chloride | TMS | Cl-TMOS | TMOS | Propyl-TMS | Cl-CPTMS | CPTMS | Bis TMS Propane |
|---|---|---|---|---|---|---|---|---|
| 0.000 ± 0.000 | 0.001 ± 0.001 | 3.271 ± 0.599 | 1.128 ± 0.139 | 2.537 ± 0.244 | 1.752 ± 0.210 | 0.747 ± 0.076 | 87.935 ± 0.909 | 0.728 ± 0.035 |

COMPARATIVE EXAMPLE 6

At ambient temperature, 28.73 g of trimethoxysilane (0.2328 moles) was treated with 0.033 g of a 3.85% Ru (wt/wt) methanol solution of ruthenium (III) chloride hydrate (30 ppm Ru). This trimethoxysilane solution was warmed and at 80° C., it was treated with 13.30 g of methallyl chloride (0.1454 moles). The methallyl chloride was added over one hour while maintaining the trimethoxysilane solution between 78–83° C. After this addition was completed, the reaction was maintained at 80° C. for one hour. After this time, the solution was analyzed with GC. The GC data for this reaction was:

| Methallyl chloride | Isobutyl chloride | Cl-TMOS | TMOS | Isobutyl-TMS | Cl-CIBTMS | CIBTMS | Bis TMS isobutane |
|---|---|---|---|---|---|---|---|
| 0.428 | 2.950 | 1.686 | 6.462 | 3.532 | 1.485 | 71.835 | 3.915 |

What is claimed is:

1. A process for preparing a haloorganoalkoxysilane of the formula $$(R^1)_x(R^2O)_{3-x}SiCH_2CHR^3CR^4R^5X$$

wherein $R^1$ in an alkyl of from 1 to 6 carbon atoms, $R^2$ is an alkyl of from 1 to 6 carbon atoms, $R^3$ is an alkyl group of 1 to 6 carbon atoms or hydrogen, $R^4$ is an alkyl of from 1 to 6 carbon atoms, hydrogen or halogen, $R^5$ is hydrogen or an alkyl of from 1 to 6 carbon atoms, X is a halogen, x is 0, 1 or 2, which comprises reacting an olefinic halide of the general formula:

$$H_2C=CR^3CR^4R^5X$$

wherein $R^3$, $R^4$, $R^5$ and X have the aforestated meanings, with a molar excess of alkoxysilane of the general formula:

$$(R^1)_x(R^2O)_{3-x}SiH$$

wherein $R^1$ and $R^2$ and x have the aforestated meanings, in a reaction medium to which has been added a catalytically effective amount of ruthenium-containing catalyst and an electron-donating aromatic compound in an amount of about 1 to about 100 mole equivalents versus the moles of ruthenium metal; wherein the yield of the haloorganoalkoxysilane exceeds 87 mole percent, based upon the total reaction products.

2. The process of claim 1, wherein the olefinic halide is selected from the group consisting of allyl chloride, methallyl chloride, 3-chloro-1-butene, 3, 4-dichloro-1-butene and 2-chloropropene.

3. The process of claim 1, wherein the alkoxysilane is selected from the group consisting of trimethoxysilane, methyldimethoxysilane, dimethylmethoxysilane, triethoxysilane methyldiethoxysilane, dimethylethoxysilane, ethyldiethoxysilane, and diethylethoxysilane.

4. The process of claim 1, wherein the olefinic halide is allyl chloride and the alkoxysilane in diethylethoxysilane.

5. The process of claim 1, wherein the cumulative mole ratio of alkoxysilane to olefinic halide ranges from about 1.3 to about 3.0.

6. The process of claim 1, wherein the cumulative mole ratio of alkoxysilane to olefinic halide ranges from about 1.8 to about 2.3.

7. The process of claim 4, wherein the cumulative mole ratio of trimethoxysilane to allyl chloride ranges from about 1.8 to about 2.3.

8. The process of claim 1, wherein the reaction is carried out at a temperature of from about 50 to about 130° C.

9. The process of claim 1, wherein the reaction is carried out at a temperature of from about 60 to about 80° C.

10. The method of claim 1, wherein the ruthenium-containing catalyst is selected from the group consisting of $RU_3(CO)_{12}$, $[Ru(CO)_3Cl_2]_2$, cyclooctadiene-$RuCl_2$, $RuCl_3$, $(Ph_3P)_2Ru(CO)_2Cl_2$, $(Ph_3P)_3Ru(CO)H_2$, Ru on Fe, Ru on $Al_2O_3$, Ru on carbon, $Ru(AcAc)_3$, and $RuBr_3$.

11. The process of claim 1, wherein the amount of ruthenium present in the reaction medium is from about 5 to about 100 ppm by weight of the reactants.

12. The process of claim 1, wherein the amount of ruthenium-containing catalyst present in the reaction medium is from about 15 to about 25 ppm by weight of the reactants.

13. The process of claim 1, wherein the electron donating aromatic compound is selected from the group consisting of benzene, ethylbenzene, diethylbenzene, triethylbenzene, n-butylbenzene, di-t-butylbenzene, bibenzyl, toluene, t-butyltoluene, anisole, 1-phenylhexane, 1-phenyldodecane, m-xylene, mesitylene, p-cymene, diphenylmethane, triphenylmethane, phenyl ether, phenothiazine, and biphenyl.

14. The process of claim 1 wherein the electron-donating aromatic compound is present in an amount of from about 5 to about 50 mole equivalents versus the moles of ruthenium metal.

15. The process of claim 1, wherein the electron-donating aromatic compound is present in an amount of from about 20 to about 30 mole equivalents versus the moles of ruthenium metal.

16. A process for preparing a chloroalkylmethoxysilane of the general formula:

$(CH_3)_x(CH_3O)_{3-x}SiCH_2CHR^3CR^4R^5Cl$ wherein $R^3$ is an alkyl of from 1 to 6 carbon atoms or hydrogen, $R^4$ is an alkyl of from 1 to 6 carbon atoms, hydrogen or chlorine, $R^5$ is hydrogen or an alkyl of from 1 to 6 carbon atoms and x is 0, 1 or 2, which comprises reacting an olefinic chloride of the general formula:

$H_2C=CR^3CR^4R^5Cl$ wherein $R^3$, $R^4$ and $R^5$ have the aforestated meanings with an excess of a methoxysilane of the general formula:

$(CH_3)_x(CH_3O)_{3-x}SiH$ wherein x has the aforestated meaning in a cumulative mole ratio of methoxysilane to olefinic chloride of from about 1.3 to about 3.0 at a temperature of from about 60 to about 130° C. in a reaction medium into which has been added a ruthenium-containing catalyst containing from about 5 to about 100 ppm ruthenium based on the total weight of the reactants and an aromatic compound of from about 1 to about 100 mole equivalents versus the moles of ruthenium metal; wherein the yield of the chloroalkylmethoxysilane is greater than or equal to about 87 mole percent, based upon the total reaction products.

17. The process of claim 16, wherein the olefinic chloride is allyl chloride.

18. The process of claim 16, wherein the methoxysilane is trimethoxysilane.

19. The process of claim 18 wherein the cumulative mole ratio of methoxysilane to olefinic chloride is from about 1.3 to about 3.0.

20. The process of claim 16 wherein the reaction is carried out at a temperature of from about 60 to about 80° C.

21. The process of claim 16 wherein the ruthenium-containing catalyst is selected from the group consisting of $RuCl_3$ hydrate, $Ru_3(CO)_{12}$ and $[RUCl_2(CO)_3]_2$.

22. The process of claim 16 wherein the reaction medium contains from about 15 to about 25 ppm ruthenium based on the total weight of the reactants.

23. The process of claim 16 wherein the olefinic chloride is allyl chloride, the methoxysilane is trimethoxysilane, the cumulative mole ratio of trimethoxysilane to allyl chloride is from about 1.4 to about 2.0, the reaction temperature is from about 60 to about 80° C., the ruthenium-containing catalyst is selected from the group consisting of $RuCl_3$ hydrate and the reaction medium contains from about 15 to about 25 ppm ruthenium based on the total weight of the reactants.

24. The process of claim 1, wherein the yield of the haloorganoalkoxysilane exceeds 90 mole percent, based upon the total weight of the reaction products.

25. The process of claim 1, wherein the yield of the haloorganoalkoxysilane exceeds 92 mole percent, based upon the total weight of the reaction products.

26. The process of claim 16, wherein the yield of the haloorganoalkoxysilane exceeds 90 mole percent, based upon the total weight of the reaction products.

27. The process of claim 16, wherein the yield of the haloorganoalkoxysilane exceeds 92 mole percent, based upon the total weight of the reaction products.

* * * * *